United States Patent [19]
Postelmans

[11] Patent Number: 5,611,774
[45] Date of Patent: Mar. 18, 1997

[54] KNEE SUPPORT OR REPLACEMENT APPARATUS

[75] Inventor: Roberto J. J. Postelmans, Brussels, Belgium

[73] Assignee: Françoise Ghislaine Dumont, Brussels, Belgium

[21] Appl. No.: 416,892

[22] PCT Filed: Oct. 22, 1993

[86] PCT No.: PCT/BE93/00066

§ 371 Date: Apr. 20, 1995

§ 102(e) Date: Apr. 20, 1995

[87] PCT Pub. No.: WO94/09729

PCT Pub. Date: May 11, 1994

[30] Foreign Application Priority Data

Oct. 23, 1992 [BE] Belgium ............................. 09200918

[51] Int. Cl.$^6$ ......................................................... A61F 5/00
[52] U.S. Cl. ................................................. 602/16; 602/26
[58] Field of Search ........................ 602/5, 16, 23, 602/26, 27; 623/27, 39–46

[56] References Cited

U.S. PATENT DOCUMENTS 3,779,654  12/1973  Horne .
4,723,539   2/1988  Townsend ................... 602/16
5,107,824   4/1992  Rogers et al. .
5,330,418   7/1994  Townsend et al. ............ 602/16 X

FOREIGN PATENT DOCUMENTS 0297766  1/1989  European Pat. Off. .
2600528  12/1987  France .
92/15264  9/1992  WIPO .

*Primary Examiner*—Linda C. Dvorak
*Attorney, Agent, or Firm*—Spencer & Frank

[57] ABSTRACT

A knee support or replacement apparatus of the asymmetrical multi-convolution type comprising at least one outer joint and one inner joint which are arranged each side of a vertical antero-posterior plane and which each comprise at least one proximal member and at least one distal member articulated together. A first connection device is for connecting together the proximal members and the distal members, and a guide device provides the articulated members, with different movements for each joint. The articulated members of each joint exhibit bearing surfaces with complex curvatures different from each other by means of which they are in only partial contact, at at least three points.

14 Claims, 14 Drawing Sheets

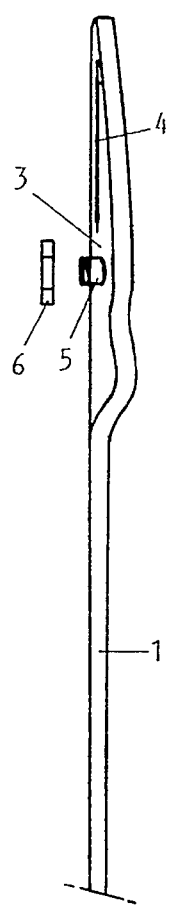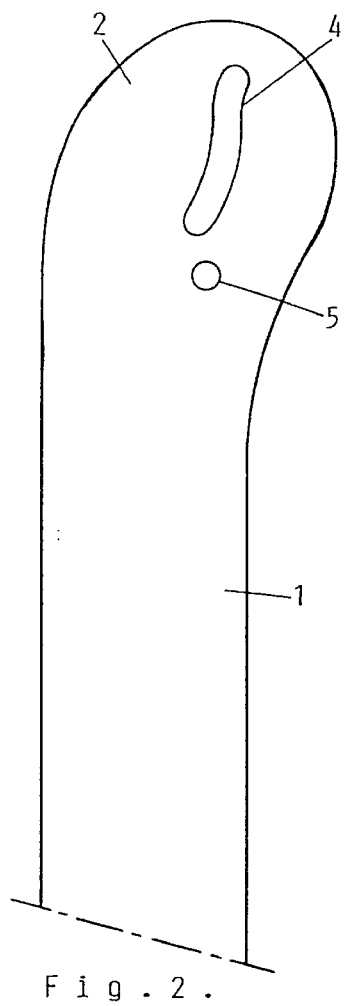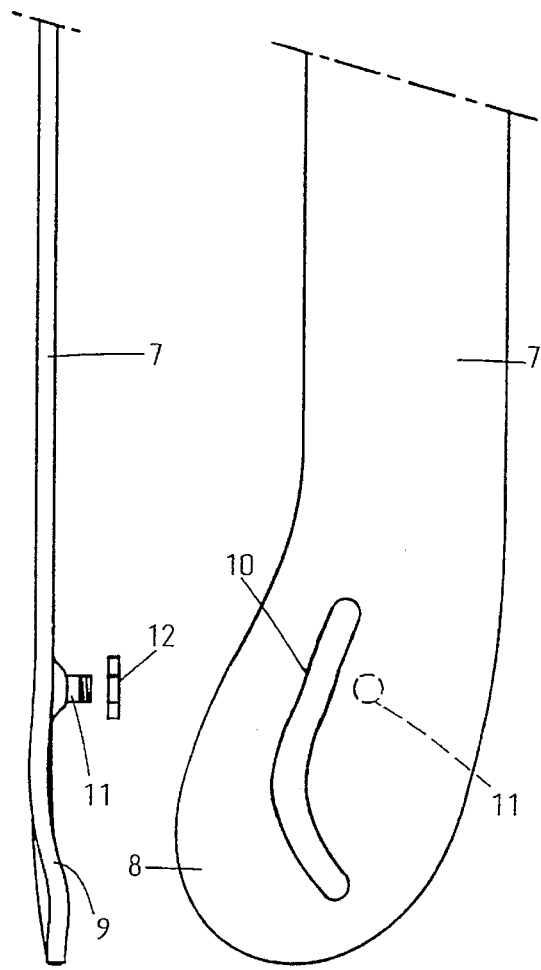
Fig. 3.  Fig. 2.  Fig. 5.  Fig. 4.

5,611,774

KNEE SUPPORT OR REPLACEMENT APPARATUS

BACKGROUND OF THE INVENTION

The present invention relates to a knee support or replacement apparatus comprising at least one outer joint and one inner joint which are arranged each side of a vertical, antero-posterior plane and which each comprise at least one proximal member and at least one distal member articulated together, first connection means for connecting together the proximal members of the joints and second connection means for connecting together the distal members of the joints, the connection means effecting mutual positioning of the joints along a common axis, attaching means for fixing the proximal members to a femoral part of a lower member and the distal members to a tibial part of said lower member, and means of guiding the pieces articulated together, enabling relative flexion movement, antero-posterior rolling connected with sliding, rotation and/or varus movement between said femoral and tibial parts, the guide means providing the members of each of said joints with a movement different from that of each of the other joints, said guide means of each joint comprising at least one guide surface of predetermined curvature in an articulated member and at least one corresponding follower element on the other articulated member, these articulated members of each joint further exhibiting bearing surfaces of predetermined curvature which cooperate during said relative movement between the femoral and tibial parts.

According to the invention, what is meant by knee support apparatus is a knee orthesis and what is meant by replacement apparatus is a knee prosthesis or endoprosthesis.

In the following, what should be understood by femoral and tibial parts of a lower member is not only the parts of an existing member but also rigid upper and/or lower members replacing this member.

Thus, the proximal member may conform to an upper rigid member fixed to the femur, or it may extend along the femur and be fixed there and the distal member may conform to a rigid lower member fixed to the tibia or it may extend therealong and be fixed there.

Also in the following, what should be understood by flexion and extension is a relative movement between the femoral and tibial parts of a member about a substantially horizontal axis passing through the knee approximately from left to right. What is to be understood by rotation is a relative movement between these parts about a vertical axis. What is to be understood by varus movement is a relative movement between these parts about a horizontal antero-posterior axis. Finally, what should be understood by sliding and antero-posterior rolling is a relative movement between the ends of the tibial and femoral parts in an antero-posterior plane.

The ortheses are orthopaedic apparatuses which enable movement and articulation of a deficient member of a handicapped person. Such apparatuses consist of two rigid parts connected together by a joint at the knee, on one side of the leg or on both sides. The whole may be fixed by bands or boxes which run along the thigh and the leg. Ortheses used for the lower members currently have two symmetrical joints at the knee, which joints allow them only a flexion movement and at best simultaneous antero-posterior displacement of the proximal part on the distal part (c.f. EP-A-0297766, U.S. Pat. No. 3,779,654). However, physiological movement of the knee is three-dimensional and these ortheses inevitably cause stress to the ligaments, which runs counter to medical or surgical treatment.

Moreover, there are known multiaxial ortheses provided with interacting slotted planar plates successively permitting rearwards sliding of the tibia with respect to the femur at the start of flexion and then rotation (WO-A-92/15264).

There also exists a polyaxial knee protector which is three-dimensional (c.f. Poli-Axial knee protector by Generation II Orthotics, Inc., Vancouver, Canada) and which comprises a joint for fitting on one side of the deficient knee. In this joint, two segments of a sphere interact, said segments having two slots forming arcs of a circle arranged about an axis in offset manner. In the first degrees of flexion the proximal member moves, and, when it has reached the end of the range of its slots, flexion continues over the slot of the second segment of a sphere, thus giving three-dimensional movement, but not physiological movement. In fact, the physiological movement of the knee exhibits, owing to a system of ligament links, movement consisting of antero-posterior rolling and of sliding connected with rotation and varus movement. The rotation and varus movement occur, according to the majority of medical studies, mainly at the beginning of flexion, which this known apparatus does not permit.

An orthesis is also known as described at the start (U.S. Pat. No. 5,107,824), in which the guide means are formed of slotted spherical shells interacting together. Given that the centre of the shells of the outer joint of this apparatus is situated at a different point from the centre of the shells of the inner joint, blockage of the apparatus inevitably occurs since the outer and inner shells are also connected together firmly by rigid bands around the thigh and the leg. Moreover, the spherical shape of the shells and their intimate support one on another prevents the obtaining of a movement with a complex trajectory permitting following of the physiological movement of the knee.

Prostheses are orthopaedic apparatuses which enable persons who have lost all or part of their leg to walk. These apparatuses surmounted by a socket allow the disabled person to lean on his stump and a joint, situated at the knee axis, permits flexion of the prosthesis. For femoral prostheses for full amputation or for knee disarticulation it is impossible to position the prosthetic joint at its physiological point. The prosthetic joint is positioned lower than the physiological knee axis, which renders walking uncomfortable and gives the seated position an unaesthetic appearance, the thigh part being abnormally longer than the tibia part.

SUMMARY OF THE INVENTION

The present invention aims to perfect an improved knee support or replacement apparatus, which enables control of the three-dimensional movement with sliding and antero-posterior rolling, associated with rotation and varus movement of the tibial and femoral parts, the whole being perfectly connected during flexion or extension of the leg. Moreover, the apparatus according to the invention should preferably be of very low bulk and not cause any discomfort when in operation.

The present invention also aims to avoid the disadvantages mentioned above.

Thus there is provided, according to the invention, a knee support or replacement apparatus as described above and characterized in that said bearing surfaces of the guide means of each joint exhibit mutually different complex curvatures by means of which they are in only partial contact, at at least three points, during movement between the femoral and tibial parts.

As has already been described, the physiological movement of the knee consists of several simultaneous movements, which is made possible by a special configuration of the ends of the bones and by connection thereof by cruciate ligaments.

If reference is made to the attached FIG. 1, an illustration may be seen of a plane XOY representing the central antero-posterior plane of a left knee, seen from the back. In the position shown, the cruciate links AO and BC represent schematically the above-mentioned cruciate ligaments in the leg extension position. Reference letter a designates the anterior cruciate ligament and reference letter c the posterior cruciate ligament. Reference letter b (AB) represents the intercondylar area and reference letter d (CO) the tibial plate. The angle σ is the angle of inclination between the intercondylar area and the plane parallel to the plane ZOX, through which passes the axis 50, which itself passes through A.

According to certain theoretical studies, rotation of the knee is effected, at the same time as flexion, about a substantially vertical axis (O'Y') situated in a plane, known as a pivot plane, itself arranged slightly inwards with respect to the central plane. The varus is effected about the axis O'X' situated in this same pivot plane. In FIG. 1 the knee shown is a left knee, the inside of the knee being to the right in the drawing and the pivot plane Y'O'X' thus being offset by a small distance dl with respect to the central plane YOX.

Application of two identical link mechanisms each side of the knee, in the same axis as the knee, can only give rise to flexion about the axis OZ, without rotation or varus. The arrangement of the links optionally additionally permits sliding and antero-posterior rolling. The invention consists in perfecting a knee support or replacement apparatus comprising guide means which provide the articulated members with movement of the type obtained by two different linkage mechanisms each side of an antero-posterior plane.

To illustrate this arrangement, one could imagine a car on which there have been put, on the same axle, two front wheels, the right-hand of which, for example, is larger than the left-hand. This car will necessarily turn to the left, about a single centre for all the car, in a manner controlled by the diameter of each wheel. It is also possible to envisage, along this axle, an infinity of wheels which each have a different radius according to their position, to conform to the general movement.

As may be easily understood from FIG. 1, in each plane parallel with the central antero-posterior plane separating towards Z, the linkage mechanism must permit a movement of a larger radius to permit simultaneously the rotation and varus movements about their corresponding axes situated in the pivot plane and a smaller radius movement will be provided in each plane parallel with the central plane in the opposite direction.

Finally, this movement of the linkage mechanism type must lie within complex curved surfaces to permit without difficulty simultaneous rotation and varus movements. In effect, it is necessary to take into account, as has already been said, that these rotation and varus movements, if they are simultaneous principally at the start of flexion, vary in amplitude as flexion occurs, and each differently time-wise.

It appears that the application of simple slotted planar plates or slotted spherical caps, articulated one inside the other and resting on each other over their entire surfaces, did not permit accompanying of this irregular movement and of necessity at some point or other the orthetic apparatus was bound to lock or the knee had to be forced by maladjusted guidance of the interacting planar or spherical surfaces.

According to an improved embodiment of the invention, the articulated members of a joint each comprise, at a first end, at least one shell provided with at least one slot and/or at least one follower element capable of sliding in a slot in the other articulated member, and at least one shell of one of the articulated members comprises a bearing surface exhibiting a first predetermined complex curvature with which a bearing surface exhibiting a second complex curvature, different from the first, of at least one shell of the other articulated member may cooperate by said partial contact during said relative movement between the femoral and tibial parts. To permit rotation and varus of the knee, in the case of use according to the invention of different linkage mechanisms each side of the knee, it is necessary, to prevent locking of the linkage mechanisms, to provide them with a certain play. Unfortunately, this can only be done with a certain loss of control of the knee movement. This is why, according to a preferred embodiment of the invention, mechanisms are used which provide the articulated members with movement of the type obtained by a linkage mechanism, while being perfectly spatially controlled. These mechanisms may, for example, comprise cams, preferably slotted cams, and cam follower elements, tensioned cruciate straps or any similar articulation. The slots or guide surfaces are formed in three-dimensional cams. The slotted cams are thus preferably in the form of shells of complex curvature predetermined in accordance with the movement to be obtained.

It should be noted in this connection that specialists do not always agree on the movements which are produced during flexion of a knee or in any case on their amplitude at the moment of their production. Moreover, each patient has knees with differing parameters. The shape and curvature of the slots and shells must be calculated in accordance therewith, as must their area of partial contact during their interaction.

According to one embodiment of the invention, the above-mentioned vertical antero-posterior plane passes through the knee. In the case of an orthesis, the outer joint is advantageously on the outside of the knee and the inner joint on the inside of the knee. The joints will thus here be either side of the pivot plane.

According to another embodiment of the invention, the above-mentioned vertical antero-posterior plane is arranged on one side of the knee. In fact, it is possible to imagine that the outer joint and the inner joint may both be one and the same side of the knee.

According to yet another embodiment of the invention, the proximal members of the outer and inner joints form a one-piece element, the distal members of these joints also form a one-piece element and the two one-piece elements are articulated together by said guide means.

BRIEF DESCRIPTION OF THE DRAWINGS

Other details and characteristics of the invention will become apparent from the description given below by way of non-limiting example and with reference to the attached drawings.

FIGS. 2 to 5 show, in elevation and in profile, the articulated members of an inner joint of a left orthesis according to the invention.

DETAILED DESCRIPTION OF THE INVENTION

Figure 1:
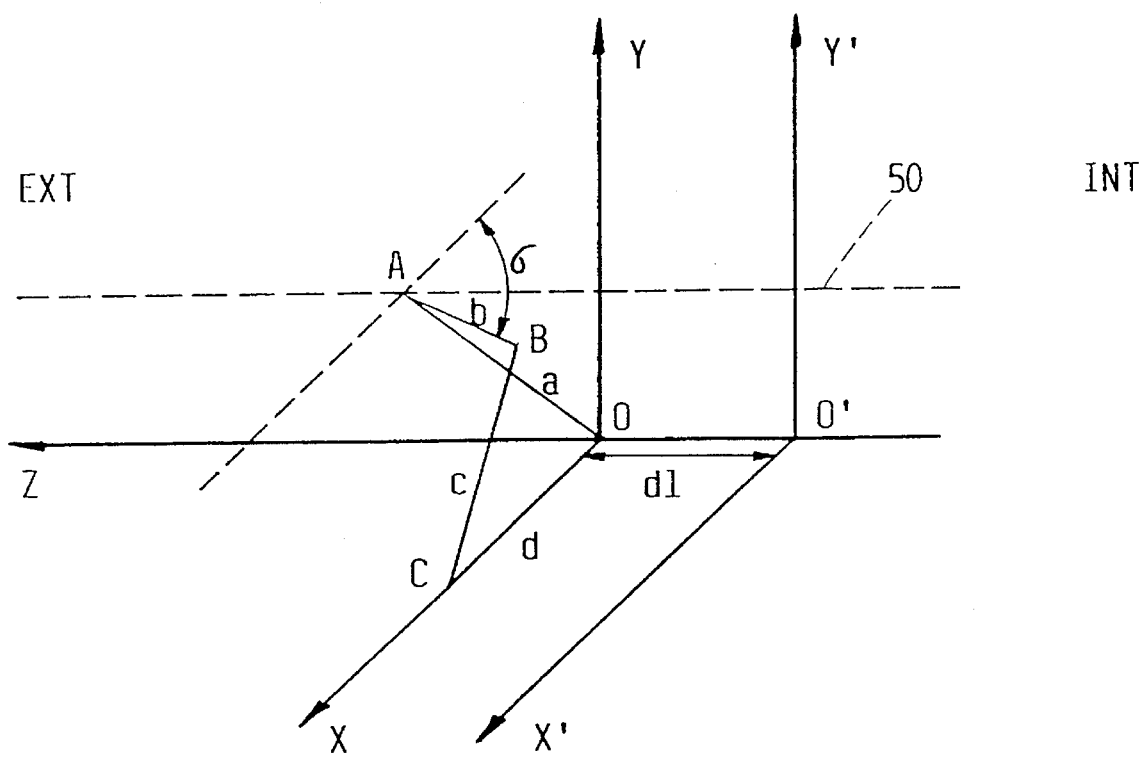
FIG. 1 is a schematic representation of a cruciate linkage mechanism of a left knee joint.

FIGS. 2 and 3 show views in elevation and in profile of the distal member of the inner joint of this orthesis. This distal member is formed of a rod 1, one end, the proximal end, of which widens to form a shell 2 with a curved outer surface 3 of predetermined curvature. This shell 2 is provided with a guide slot 4 of predetermined curvature and a stud 5 projecting laterally with respect to the curved surface 3. In this embodiment this stud is threaded and a nut 6 may be screwed thereonto.

FIGS. 4 and 5 show views in elevation and in profile of the proximal member of the inner joint of this orthesis. This proximal member is formed of a rod 7, one end, the distal end, of which widens to form a shell 8 with a curved inner surface 9 of predetermined curvature. This shell 8 is provided with a guide slot 10 of predetermined curvature and a stud 11 projecting laterally with respect to the curved surface 9. In this embodiment this stud is threaded and a nut 12 may be screwed thereonto.

Figures 6, 7, 8, 9:
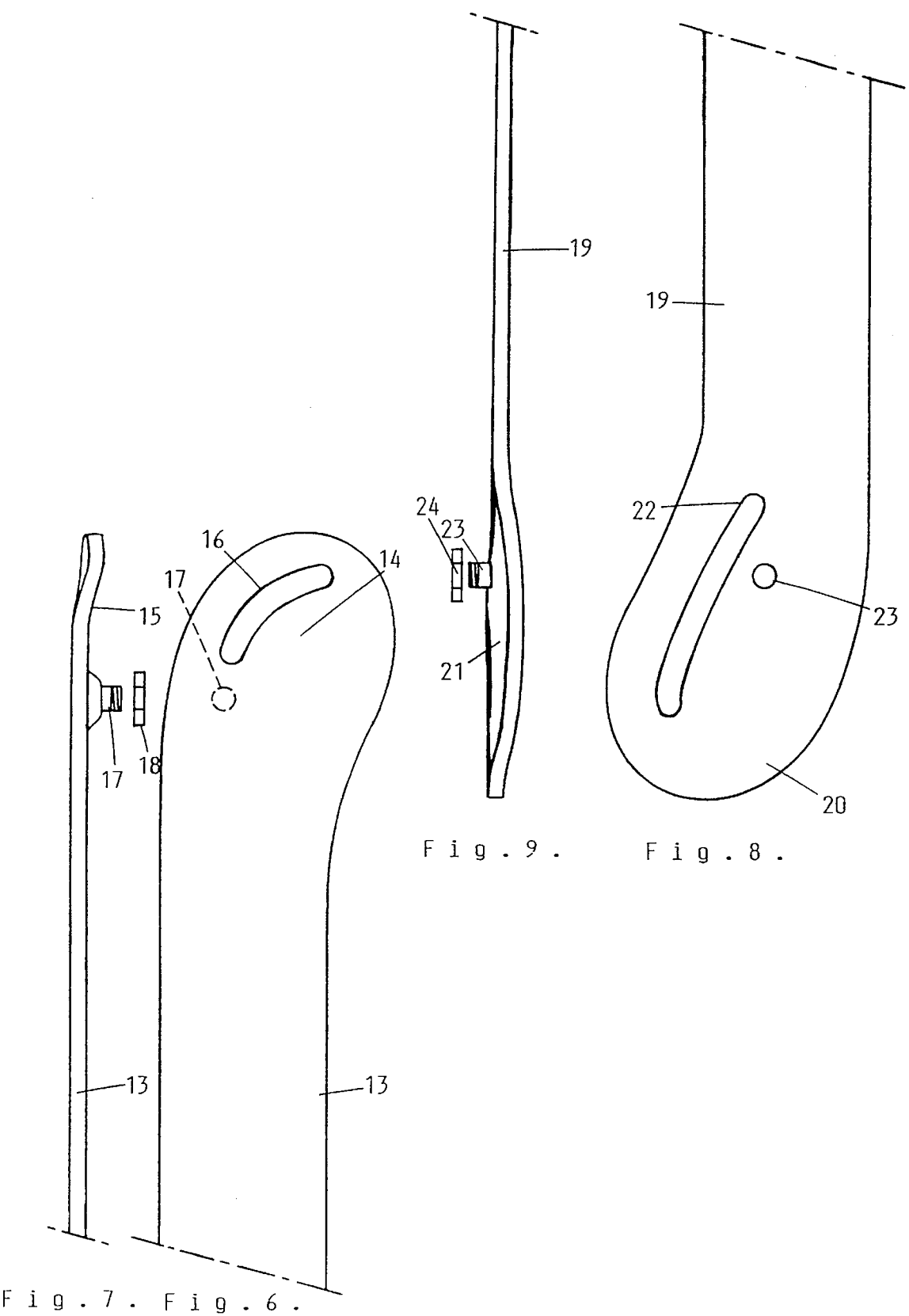
FIGS. 6 to 9 show, in elevation and in profile, the articulated members of the outer joint of this orthesis.

FIGS. 6 and 7 show views in elevation and in profile of the distal member of the outer joint of this orthesis. This distal member is formed of a rod 13, one end, the proximal end, of which widens to form a shell 14 with a curved outer surface 15 of predetermined curvature. This shell 14 is provided with a guide slot 16 of predetermined curvature and a stud 17 projecting laterally with respect to the curved surface 15. This stud 17 is here also threaded and a nut 18 may be screwed thereonto.

FIGS. 8 and 9 show views in elevation and in profile of the proximal member of the outer joint of this orthesis. This proximal member is formed of a rod 19, one end, the distal end, of which widens in the form of a shell 20 with a curved outer surface 21 of predetermined curvature. This shell 20 is provided with a guide slot 22 of predetermined curvature and a stud 23 projecting laterally with respect to the curved surface 21. This stud 23 is here also threaded and a nut 24 may be screwed thereonto.

Figure 10:
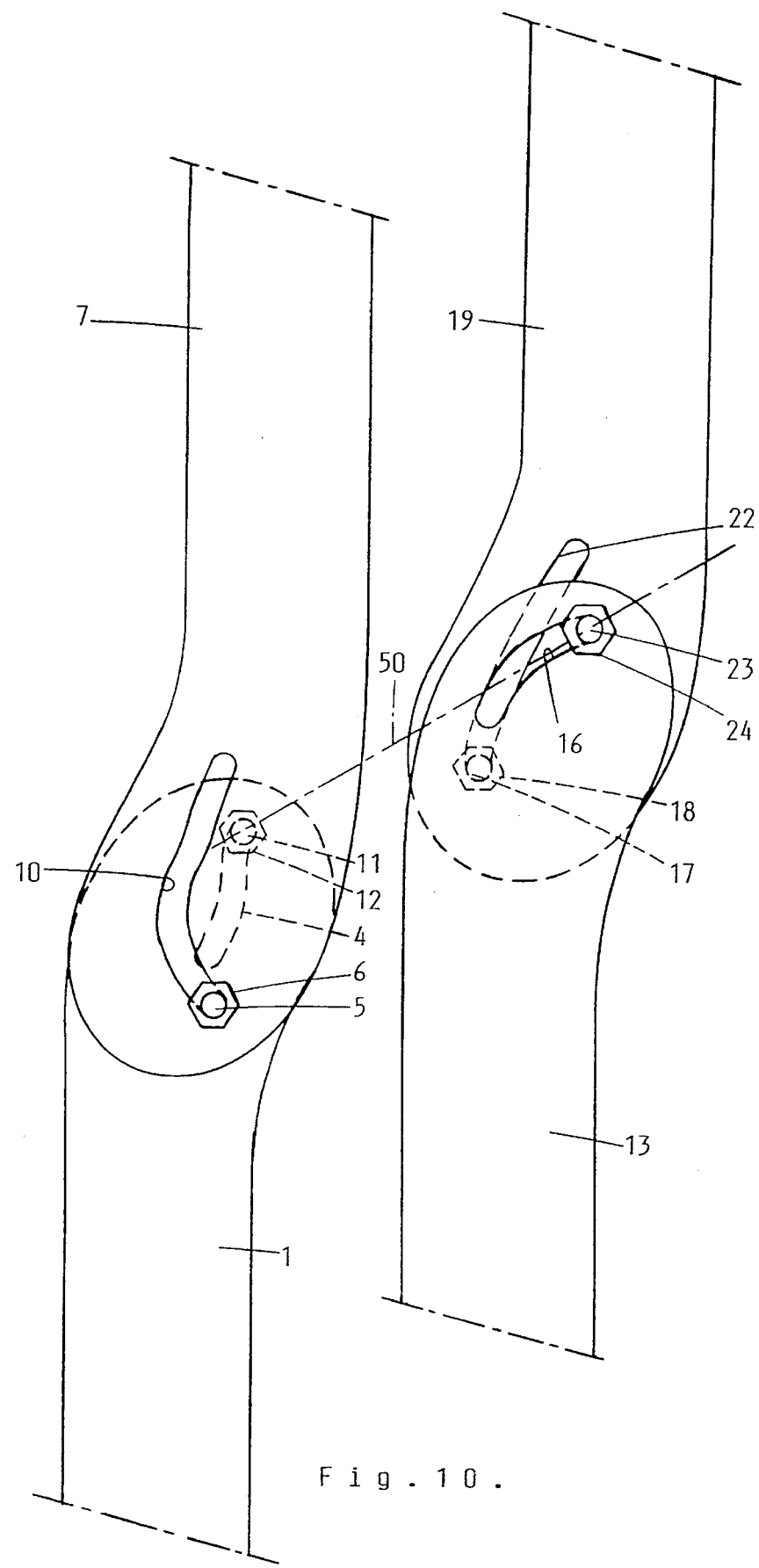
FIGS. 10 and 11 are elevational views, from the median plane, of the two joints in the assembled state, one in the extended position and the other after flexion of approximately 40°.
Figure 11:
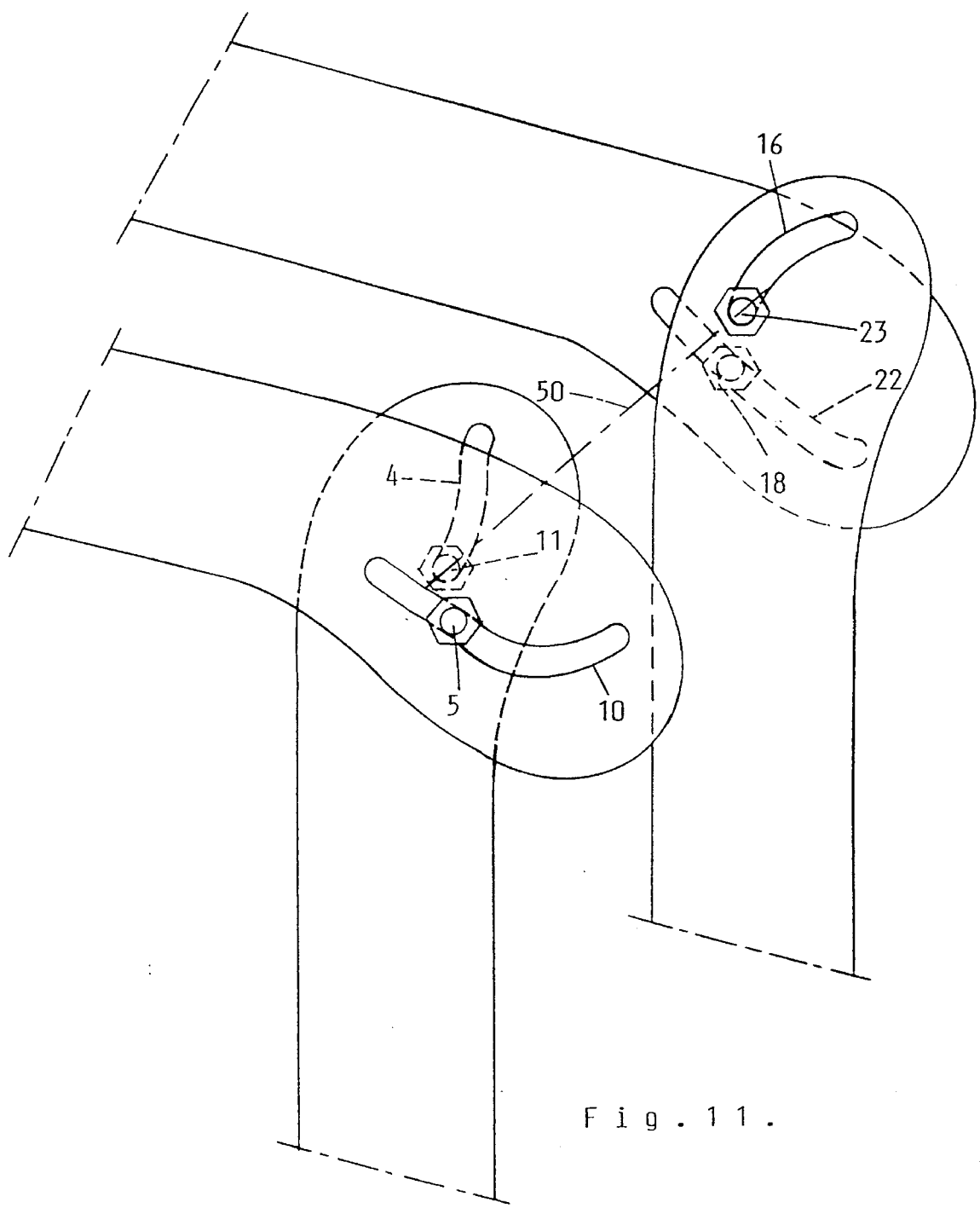

FIGS. 10 and 11 are views in false perspective of the joints in the assembled state. The two joints are shown in these two Figures in an elevational view from the median plane of the body and they are shown side by side, the inner joint on the left and the outer joint on the right.

It should be noted that, in all the Figures showing the knee support or replacement apparatus according to the invention in the assembled state, for reasons of ease only the distal member is shown in a straight invariable position and the proximal member moves with respect thereto.

In the assembled state and when the apparatus is in the extended position, in the inner joint the stud 5 is in the slot 10, at one end thereof, and it passes through the shell 8, while the stud 11 enters the slot 4 at one end thereof and passes through the shell 2. The two shells are held opposite one another by nuts 6 and 12 which are screwed onto the projecting ends of the studs 5 and 11. Similarly, in the outer joint, the stud 17 is located in the slot 22, at one end thereof, and it passes through the shell 20 while the stud 23 is located in the slot 16, at one end thereof and passes through the shell 14.

The two joints in FIG. 11 are also shown in the assembled state, but after flexion of approximately 20°. In the case illustrated, the stud 11 is then near the other end of the slot 4 and the stud 5 is approximately at the ⅔ point of the trajectory of the slot 10. Similarly, the stud 23 is near the other end of the slot 16 and the stud 18 is approximately at the ⅔ point of the trajectory of the slot 22. As may be noted, the parts of the slots 10 and 22 which the studs 5 and 18 have not yet travelled through are substantially rectilinear. This means that, in the present exemplary embodiment, from a given moment the joints will merely follow a flexion movement with sliding and antero-posterior rolling. In fact, in this exemplary embodiment the guide slots of the shells during the first two thirds of their trajectory and the positioning of the studs acting as follower elements have been calculated in accordance with the movement to be obtained, which movement is of the type obtained by a linkage mechanism with two links. The movements obtained by these means of guiding the articulated members are different for the inner joint and the outer joint. Thus, during the first 20 degrees of flexion, rotation and varus movements are simultaneously imposed by the apparatus, in the exemplary embodiment shown.

Figure 12:
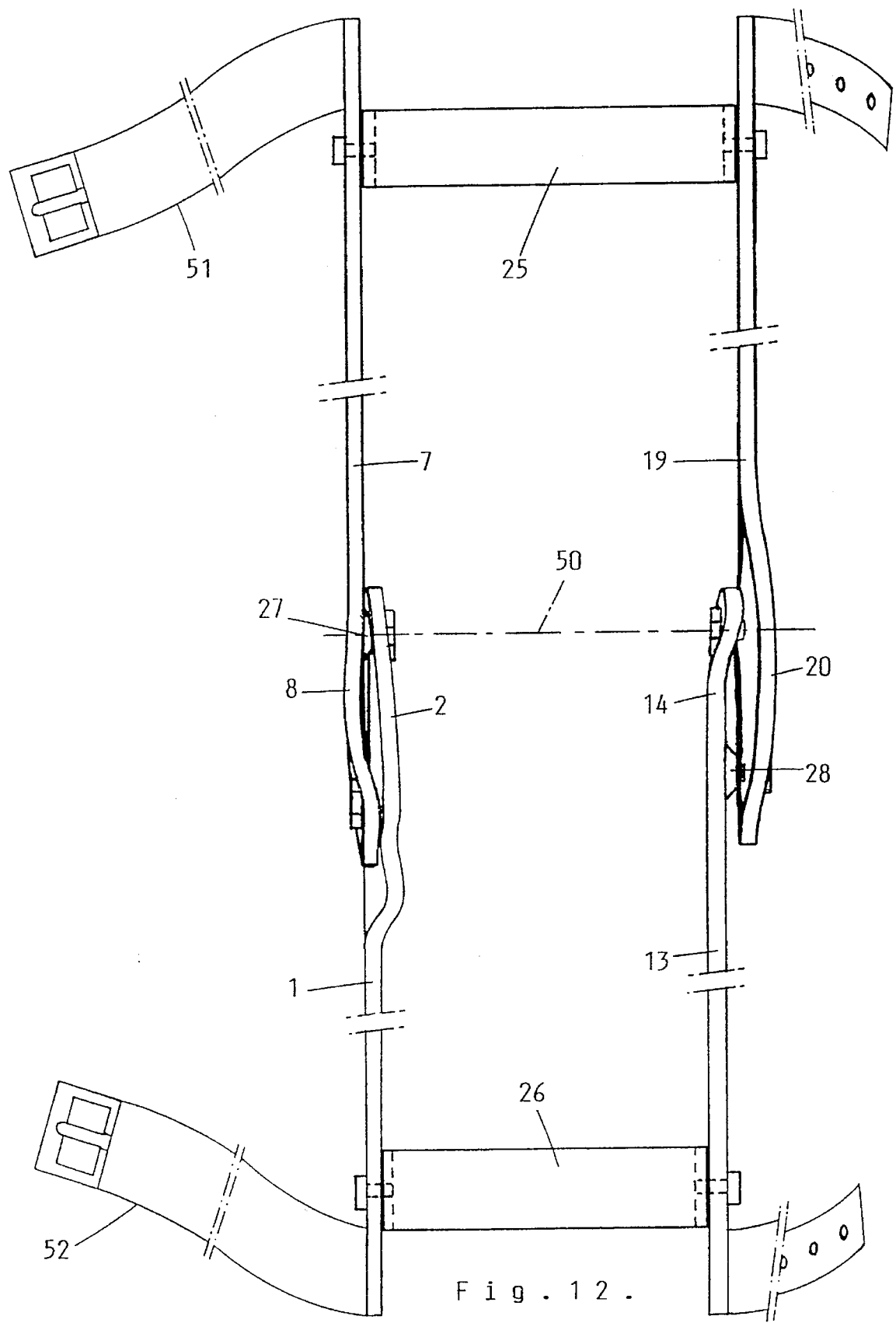
FIGS. 12 and 13 are front views of the orthesis, in extended position and in a position of approximately 40° flexion.

As may be seen from FIG. 12, the ends of the proximal and distal members of the two joints of the orthesis, which are opposite the shells, are connected together by connecting means. These allow mutual positioning of the joints in such a way that they are arranged along a common axis. In the exemplary embodiment illustrated these connecting means consist of rigid bands 25 and 26. In this position the common joint axis in this exemplary embodiment is shown in broken lines and designated by the reference numeral 50 (see also FIGS. 1, 10 and 11, from which it may be seen that this axis also moves during flexion or extension).

It goes without saying that these connecting means may have various forms. For example, an embodiment may be imagined in which the connecting means and the proximal or distal members are made in one piece.

In a known way, attaching means, straps 51 and 52 in the example illustrated here, enable fixing of the knee replacement apparatus to the thigh and leg of the patient.

The curvatures of the shells of each joint are different, and they cannot be in contact with each other over the whole of their surfaces which face each other. At all times during flexion and extension movements, the two shells rest against each other at at least three points. Taking the example of the inner joint of the orthesis shown, the bearing surfaces of the two shells 2 and 8 are situated near the stud 5 where it is situated in the slot 10, near the stud 11 where it is situated in the slot 4 and, in the extended position for example (see FIG. 12), at the lower end of the shell 8 which is in contact with a lateral bulge of the shell 2. Given that at these points friction is more intense, it is advantageously necessary to ensure that at least these partial bearing surfaces between the shells exhibit effective resistance to wear. In particular, it is possible to provide one or both of the shells with extra thickness in places, such as the extra thickness 27 and 28 in shells 8 and 14 respectively.

As may be seen from FIG. 12, in the extended position the proximal members 7 and 19 are, in this example, parallel with the distal members 1 and 13.

Figure 13:
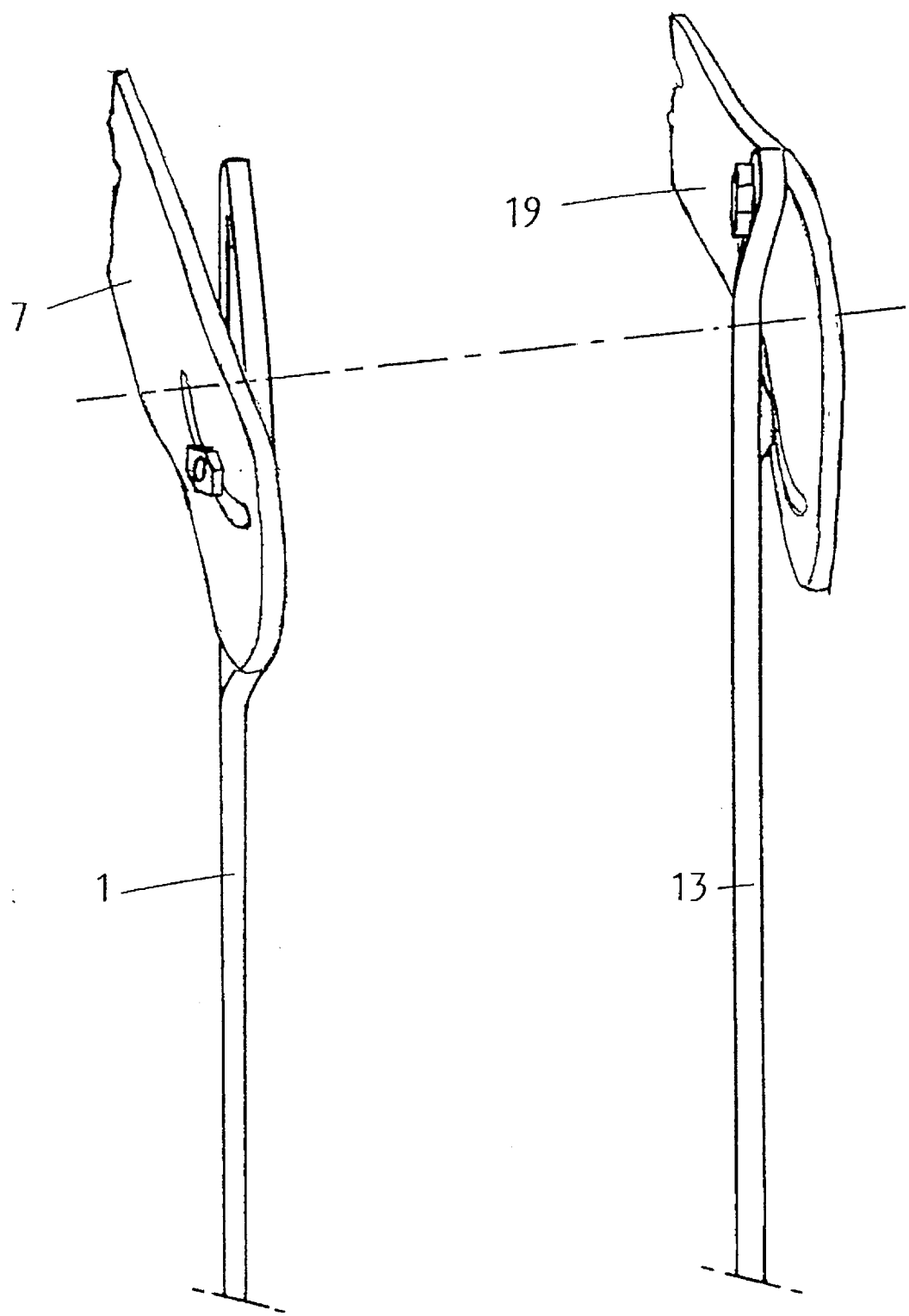

In FIG. 13, which shows, as does FIG. 12, a front view of the apparatus according to the invention but after flexion of approximately 40°, the proximal members 7 and 19 have effected, in addition to the flexion, antero-posterior rolling, sliding, rotation and a varus movement. In fact, it may be seen from this Figure that the proximal members 7 and 19 have swung downwards and towards the left in the drawing about an antero-posterior axis, not shown, which is perpendicular to the drawing.

Figure 14:
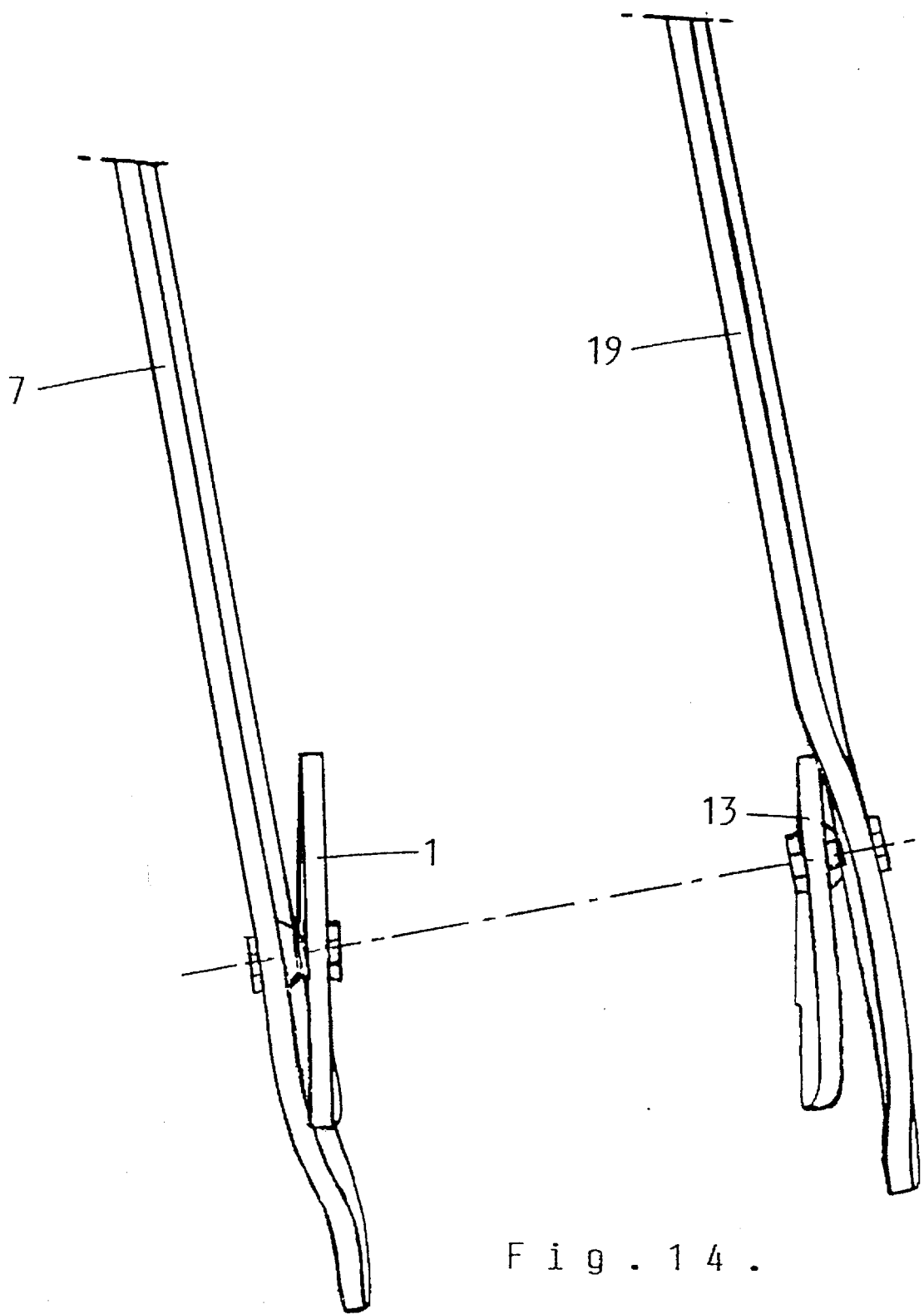
FIG. 14 is a plan view of the orthesis in a position of approximately 40° flexion.

In FIG. 14, which shows a plan view of the apparatus according to the invention, after flexion of approximately 40°, at the same time as the flexion, the antero-posterior rolling and the sliding as well as the varus movement, the proximal members 7 and 19 have effected a rotational movement. In fact, it may be seen from this Figure that the proximal members 7 and 19 have turned towards the left in the drawing about a vertical axis, not shown, which is perpendicular to the drawing.

The merely partial contact necessary between the shells during their mutual cooperation may be seen particularly well from this FIG. 14.

Figure 15:
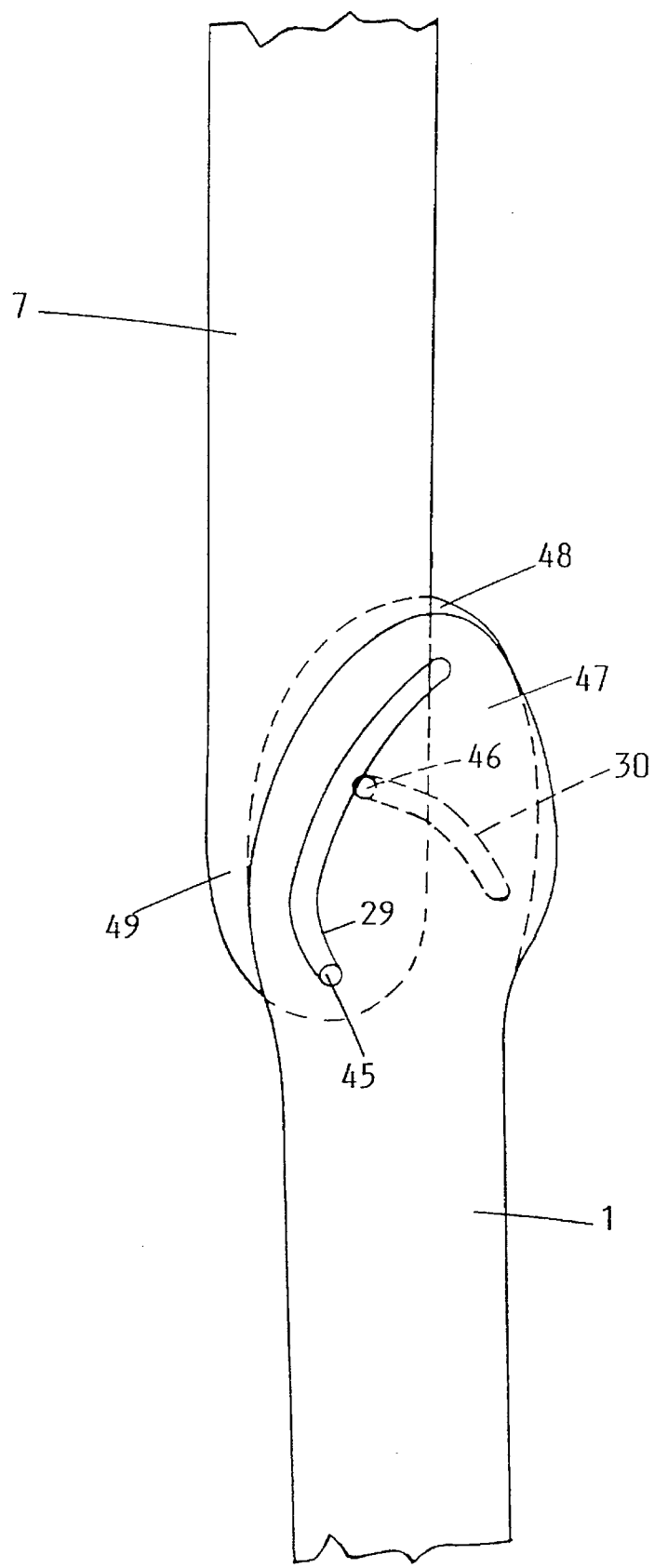
FIG. 15 is a view of a variant of the joint of an orthesis according to the invention.

FIG. 15 illustrates a variant of a joint of an apparatus according to the invention. In this exemplary embodiment the rod 1 of the distal member ends at its proximal end in the form of two shells 47 and 48 with facing surfaces of predetermined curvature. The rod 7 of the proximal member ends in a single shell 49 which is interpolated between the shells 47 and 48. The shell 49 has two surfaces of predetermined curvature capable of interacting with one of said facing surfaces of the two shells 47 and 48. In the exemplary embodiment shown the guide means consist of a first slot 29 of predetermined curvature in the shell 47, a second slot 30 of predetermined curvature in the shell 48 and two follower studs 45, 46 each projecting from one of said surfaces capable of interacting with the shell 49 and penetrating one into the slot 29 and the other into the slot 30.

It is obvious that the arrangement of the guide means may be different, for example the slots may be in the shell 49 and the studs on the shells 47 and 48. It should also be noted that the curvatures of the slots and shells must be calculated in accordance with their spatial position with respect to the antero-posterior plane known as the pivot plane. The distance between this pivot plane and each of the shells 47 and 48 is different and, to obtain a perfectly controlled joint movement according to this exemplary embodiment, it is desirable to take this fact into account when calculating the curvatures of each of the shells 47 and 48 and each of the slots in these shells.

In the exemplary embodiment illustrated in FIGS. 2 to 14, the handicapped knee is intended to be located between the outer and inner joints which are thus arranged each side of a vertical antero-posterior plane dividing the knee. However, it is possible to imagine this vertical antero-posterior plane arranged externally of the knee, laterally with respect thereto. The two joints are then on one and the same side of the pivot plane, but one of them is situated further away than the other from this plane. This implies that the guide means of the members of one of the two joints provide the latter with movement of the type obtained by a linkage mechanism different from that provided by the guide means of the members of the other joint, if it is wished to obtain perfectly controlled orthesis movement.

It is possible, for example, that the embodiment illustrated in FIG. 15 is in itself an apparatus according to the invention usable, for example as an orthesis on one side of the knee only. In fact, it may be considered that the antero-posterior plane here passes through the centre of the rod 7, the two different joints being located each side of this plane. In this example the proximal members of the two joints together form a one-piece element, that is to say the rod 7 and the shell 49.

Figure 16:
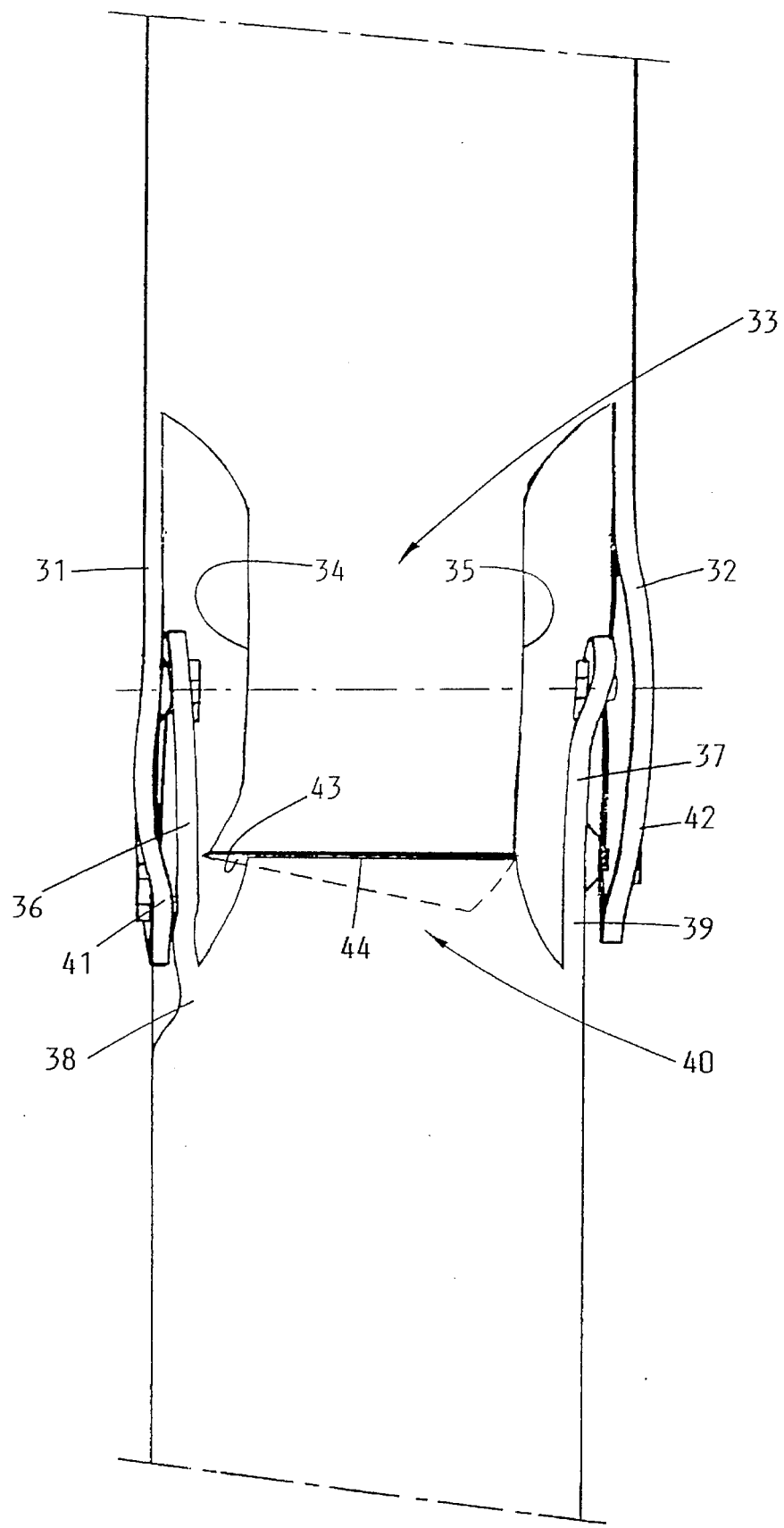
FIGS. 16 to 18 show a variant of the apparatus according to the invention adapted for a prosthesis.
Figure 17:
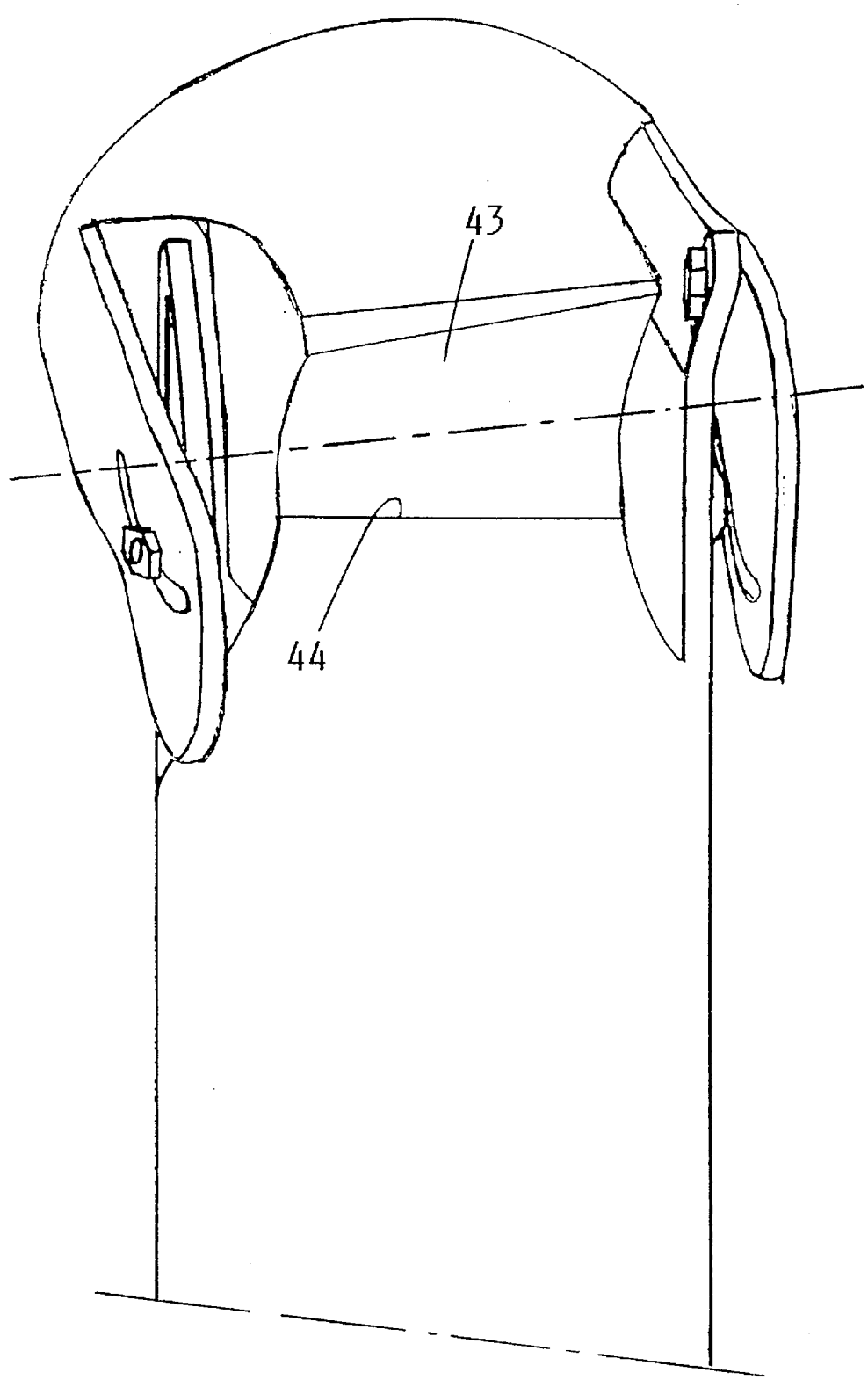
Figure 18:
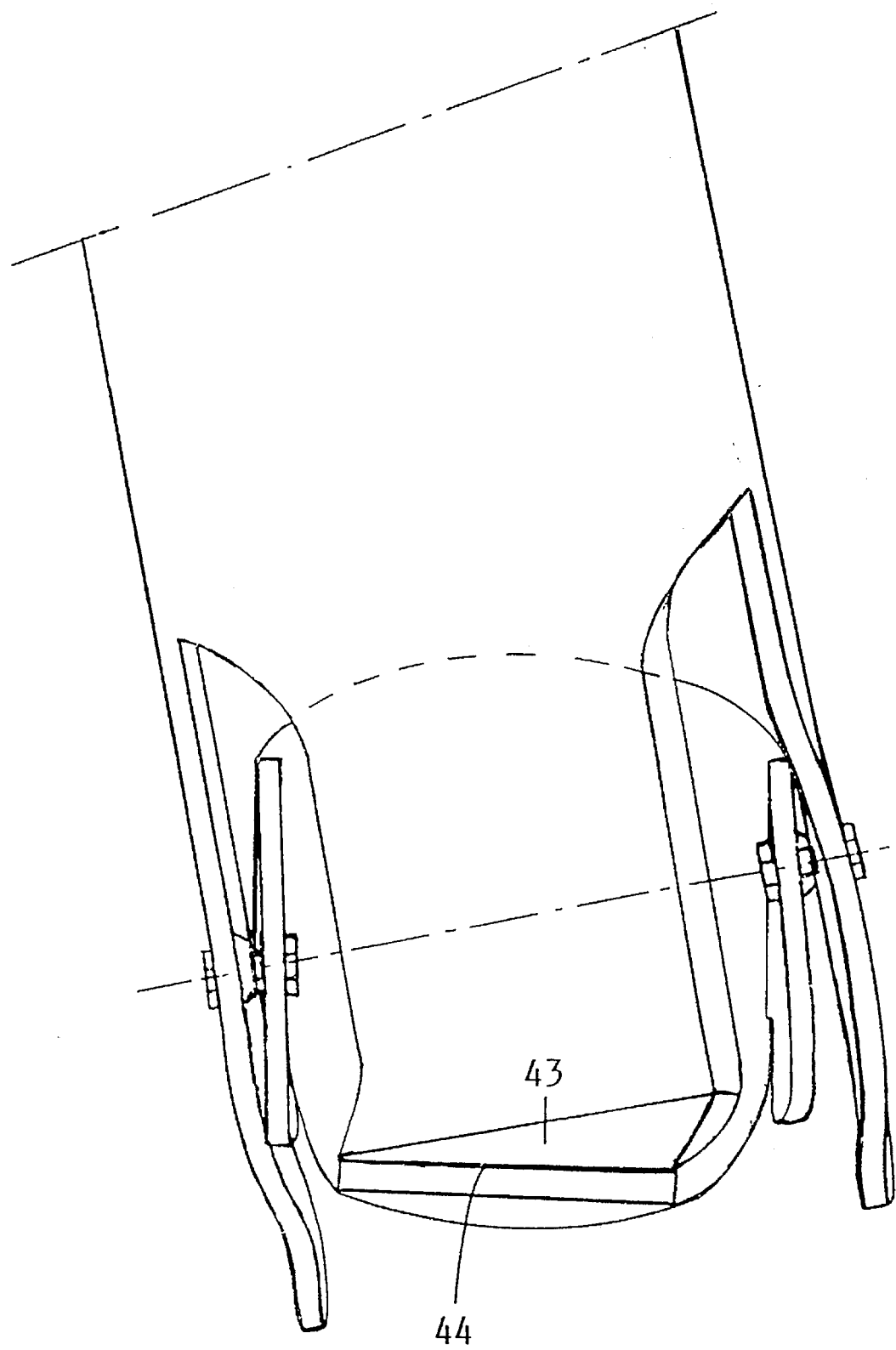

In FIGS. 16 to 18 a prosthesis apparatus is shown according to the invention in a front view in an extended state and a front view and a plane view in the flexed state, at an angle of approximately 40°.

In this exemplary embodiment the proximal members 31 and 32 of the inner joint and the outer joint together form a one-piece element with the appearance of a block 33. This block 33 has two lateral recesses 34 and 35 for the passage of the shells 36 and 37 of the distal members 38 and 39 of the inner and outer joints. In this embodiment these distal members 38 and 39 themselves also form a one-piece element having the appearance of a block 40.

The shells 41 and 42 of the proximal members and the shells 36 and 37 of the distal members are identical to those of the exemplary embodiment of an orthesis shown in FIGS. 2 to 14.

In this exemplary embodiment the two blocks 33 and 40 are in contact via the guide surfaces 43 and 44 capable of sliding over each other during movement of the joints.

It is also possible to provide in one of the blocks, for example the block 33, a guide slot passing through it from left to right with a guide surface corresponding to the guide surface 41. The artificial leg may have two shells to be arranged each side of the block 33 and to be connected by a follower shaft capable of sliding in the guide slot, two studs of the block projecting into two slots provided in said shells. The joints do not then comprise shells on the proximal members, the inner and outer parts of the block being in the form of shells at this point.

It is also possible to provide embodiments comprising a number of joints greater than two, the guide means of each joint performing a different movement in accordance with their positioning with respect to the pivot plane.

To illustrate the invention, two non-limiting exemplary embodiments of movement models to be obtained in the knee support and replacement apparatuses according to the invention are given below.

EXAMPLE 1

Parameters to be respected:

Length of the anterior cruciate ligament a: 49 mm

Length of the femoral plate b: 20 mm

Length of the posterior cruciate ligament c: 40 mm

Length of the tibial plate d: 50 mm

Angle σ: 33°

½ width of the knee: 55 mm

Situation of the pivot plane with respect to the central plane, towards the median plane: 30% of ½ width of the knee

| Evolution of the movements in accordance with flexion | | |
| --- | --- | --- |
| Flexion | Rotation | Varus |
| 10° | 3° | 2° |
| 25° | 8° | 50° |
| 45° | 11° | |
| 90° | | 7° |

EXAMPLE 2

Same parameters to be respected as for the model in Example 1, but with a different evolution of movements in accordance with the flexion.

| Flexion | Rotation | Varus |
| --- | --- | --- |
| 10° | 6° | 2° |
| 25° | 11° | 5° |
| 45° | 15° | |
| 90° | | 7° |

Figure 19:
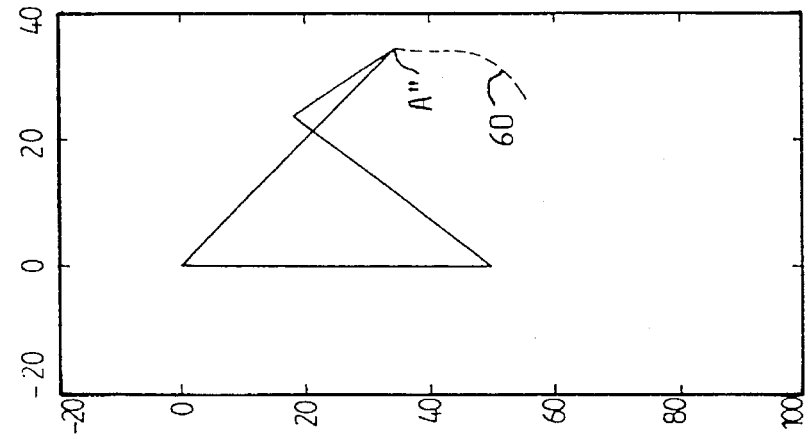

FIG. 19 shows a graph in a plane parallel to the plane XOY, situated outside the knee, in which there is illustrated the linkage mechanism of FIG. 1. To permit comparison thereof with FIG. 21, which is a plan view of a plane parallel with the plane XOZ, the graph in FIG. 19 has been turned by 90°.

The broken line designated by the reference numeral 60 shows a lateral view of the movement followed in the above-mentioned plane by the point A", situated on the axis 50 in the extended position (see FIG. 1), during the flexion of the model according to Example 1. It is possible, for example, to envisage slotting of the shell of the distal member of the outer joint in this manner.

Figure 20:
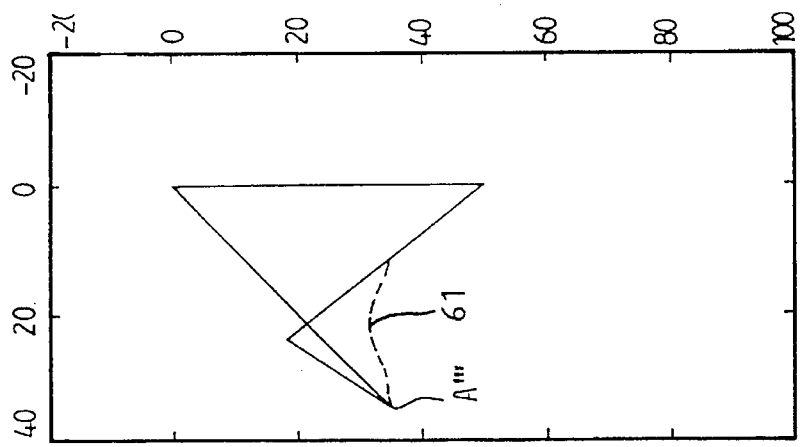
FIGS. 19 to 21 are graphs illustrating the spatial movement of the axis 50 shown in FIG. 1.

FIG. 20 shows a similar graph, but in a plane parallel with the plane XOY, situated inside the knee. The broken line designated by the reference numeral 61 shows a lateral view of the movement followed in this plane by the point A''', situated on the axis 50 in the extended position (see FIG. 1), during flexion. It is similarly possible to envisage slotting of the shell, for example, of the distal member of the inner joint in this manner.

Figure 21:
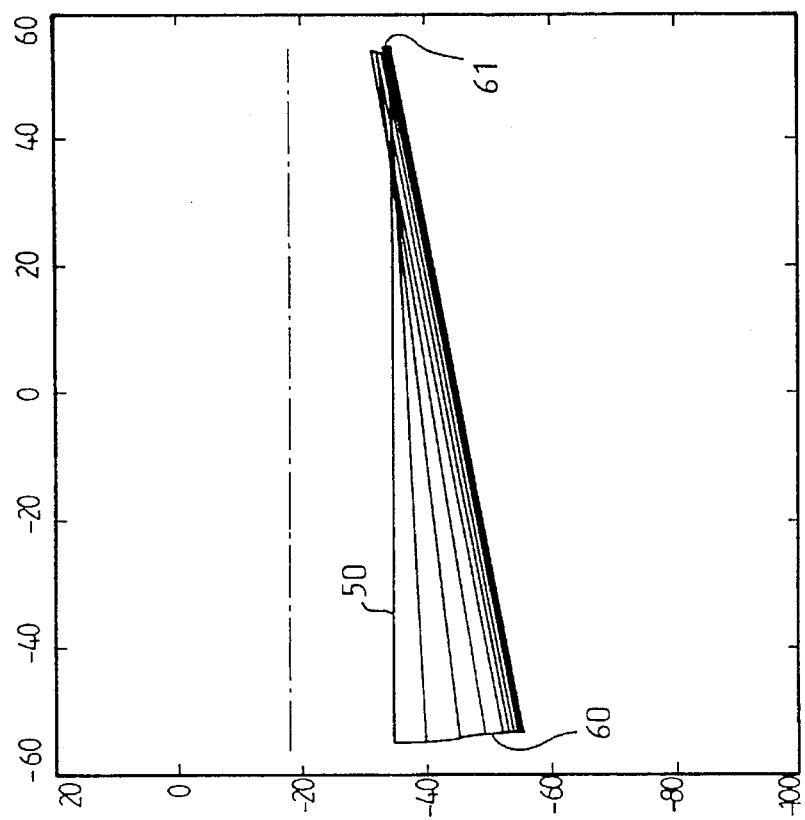

FIG. 21 shows a plan view of the fixed (tibial) part of the joint. In absciss the point 0 represents the central plane of the knee and the pivot plane is located near number 20. The axis 50, the ends of which are formed, in the example under consideration, as studs penetrating into the slots 60 and 61, effects during flexion a movement shown in FIG. 21, in which the succession of straight lines represent the successive positions of the axis 50.

As may be seen from FIG. 21, the slots 60 and 61 not only exhibit complex curvature when viewed laterally in one plane, as in FIGS. 19 and 20, but they must further be formed in surfaces which are not planar or spherical but of complex curvature.

These asymmetrical convolutions are determined by calculation in accordance with the parameters to be respected.

Figure 22:
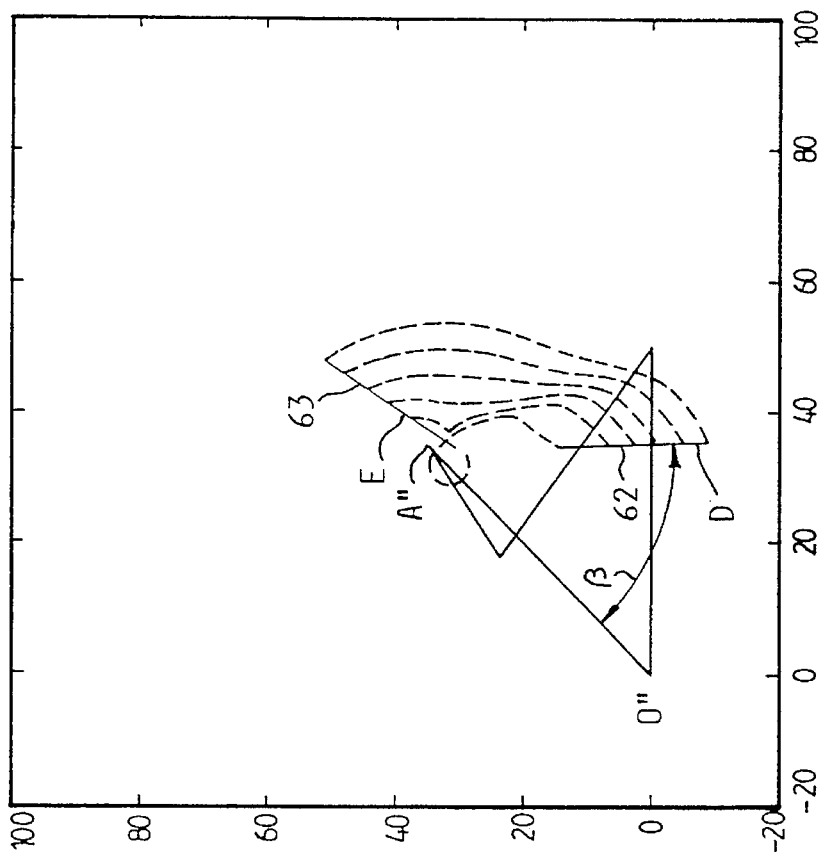
FIG. 22 shows a graph similar to FIG. 19, illustrating various embodiments of the invention.

FIG. 22 is similar to FIG. 19. However, here the point of departure (extended position) selected for the slot in the shell of the distal member, for example the outer shell, is no longer point A", but rather a point D situated on a straight line 62 oriented at angle β with respect to the straight line O"A". Depending on the position, selected on this straight line, of the point of departure, the slots will have different shapes, which are illustrated with broken lines. The ends E of all these possible slots are also situated in the graph on a straight line 63, but the curves obtained are not parallel. It is easy to understand from this graph that the number of possible shapings for the different joints is infinite.

Figure 23:
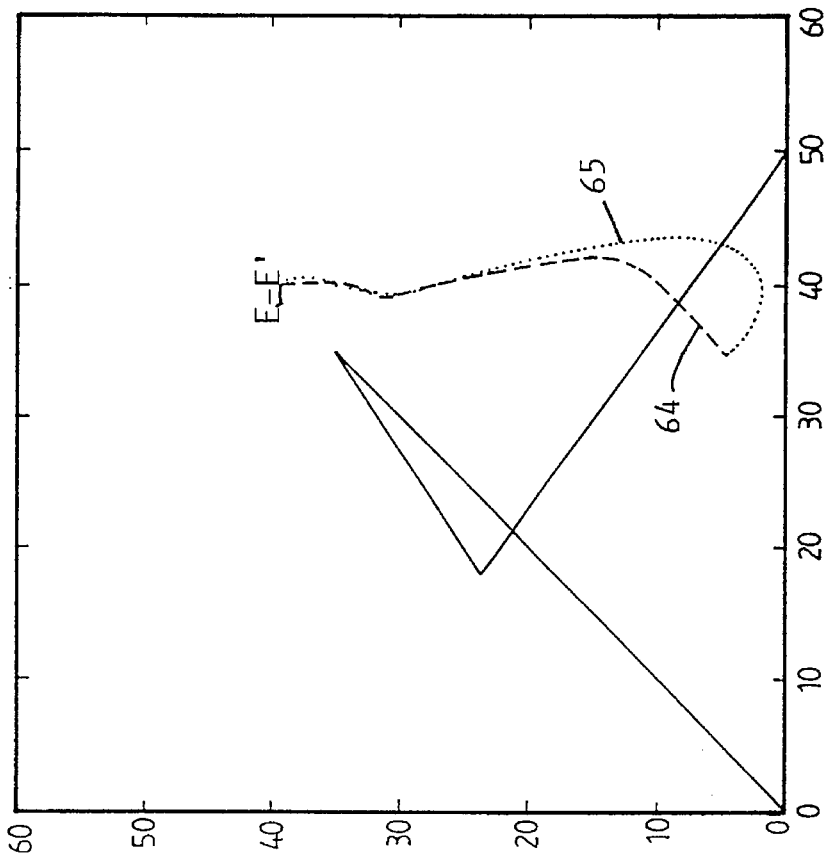
FIG. 23 shows graphically the relative movements of two points, one situated on one shell of a joint, the other on the other shell.

FIG. 23 is similar to FIG. 22, on a larger scale. It illustrates by the broken line 64 the selected slot, its point of departure D and its opposite end E. On the other shell, on the proximal member of the joint, in the extended position there exists a point E' facing the end of the slot 64 in the distal member. During flexion movement this point E' is also subjected to a movement illustrated by the dotted line 65. It may be seen that the point E' must be able to follow another trajectory than that of the slot 64, which involves shell shapes enabling only partial contact between the bearing surfaces thereof.

I claim:

1. A knee support or replacement apparatus comprising:
    at least one outer joint and one inner joint which are arranged each side of a vertical, antero-posterior plane, each joint comprising articulated members including at least one proximal member and at least one distal member articulated together,
    first connection means for connecting together the proximal members of the joints, and second connection means for connecting together the distal members of the joints, the connection means effecting mutual positioning of the joints along a common axis,
    attaching means for fixing the proximal members to a femoral part of a leg and the distal members to a tibial part of the leg,
    and guide means for guiding the articulated members together, enabling relative flexion movement, antero-posterior rolling connected with at least one of a sliding, rotating and varus movement between the femoral and tibial parts, the guide means providing the articulated members of each of the joints with a movement different from that of the articulated members of the other joint,
    said guide means for each joint comprising at least one guide surface having a predetermined curvature on one of the articulated members and at least one corresponding follower element on the other articulated member, these articulated members of each joint further comprising bearing surfaces having a predetermined curvature which cooperate during the relative movement between the femoral and tibial parts,
    said bearing surfaces of the guide means of each joint having mutually different complex curvatures by means of which the bearing surfaces are in only partial contact, at at least three points, during movement between the femoral and tibial parts.

2. An apparatus according to claim 1, wherein one of the articulated members of one of the joints comprises two guide surfaces of predetermined curvature and the other of the articulated members of this joint comprises two follower elements each capable of following one of said two guide surfaces.

3. An apparatus according to claim 1, wherein the articulated members of a respective joint each comprise, at one end, at least one shell provided with at least one of the following: at least one slot and at least one follower element capable of sliding in a slot in the other articulated member, at least one shell of one of the articulated members comprises a bearing surface with a first predetermined complex curvature with which a bearing surface comprising a second complex curvature, different from the first curvature, of at least one shell of the other articulated member may cooperate by the partial contact during the relative movement between the femoral and tibial parts.

4. An apparatus according to claim 3, wherein one of the articulated members of a joint comprises two shells which are arranged facing each other, each shell being provided with a slot and comprising bearing surfaces facing each other and having a predetermined curvature, and the other of the articulated members of this joint comprises a shell which is interpolated between the two above-mentioned shells and is provided with two follower elements each penetrating into one of said slots, and which has two bearing surfaces of curvature different from the curvatures of the bearing surfaces facing each other, these bearing surfaces each being capable of interacting by the above-mentioned partial contact with the one of said bearing surfaces facing the two shells during the relative movement between the femoral and tibial parts.

5. An apparatus according to claim 1, wherein the follower elements simultaneously act as retaining means for the articulated members articulated in partial contact one with the other.

6. An apparatus according to claim 1, wherein the vertical antero-posterior plane passes through the knee.

7. An apparatus according to claim 1, wherein the vertical antero-posterior plane is arranged on one side of the knee.

8. An apparatus according to claim 1, wherein the proximal members of the joints form a one-piece element, and the distal members of the joints are articulated to the one-piece element by said guide means.

9. An apparatus according to claim 1, wherein the distal members of the joints form a one-piece element, and the proximal members of the joints are articulated to the one-piece element by said guide means.

10. An apparatus according to claim 1, wherein the proximal members of the joints form a one-piece element, the distal members of the joints also forming a one-piece element, and the two one-piece elements being articulated to each other by said guide means.

11. An apparatus according to claim 10, wherein the two one-piece elements each have a sliding surface capable of sliding over each other during movement of the apparatus.

12. An apparatus according to claim 8, wherein the one-piece element formed by the proximal members is a block passed through laterally by an open slot on each side of the antero-posterior plane, each of the distal members having at least one follower element capable of sliding in this slot on one side of the antero-posterior plane, the slot providing, on one side of the antero-posterior plane, a first trajectory of curvature giving a predetermined movement and, on the other side of the antero-posterior plane, a second trajectory of curvature giving a predetermined movement different from that of the first trajectory.

13. An apparatus according to claim 1, wherein at least one of said first connection means and said proximal members, and said second connection means and said distal members are made in one piece.

14. An apparatus according to claim 1, wherein said guide surfaces and bearing surfaces of the guide means have predetermined curvatures to obtain a rotational movement and a varus movement about axes passing through a pivot plane arranged at a certain distance towards the inside of a central antero-posterior plane dividing the knee.

* * * * *